United States Patent
Hegde et al.

(10) Patent No.: US 7,836,888 B2
(45) Date of Patent: Nov. 23, 2010

(54) AIRWAY IMPLANT AND METHODS OF MAKING AND USING

(75) Inventors: Anant V. Hegde, Newark, CA (US); George Y. Choi, Redwood City, CA (US); Wally S. Buch, Atherton, CA (US)

(73) Assignee: Pavad Medical, Incorporated, Hayward, CA (US)

( * ) Notice: Subject to any disclaimer, the term of this patent is extended or adjusted under 35 U.S.C. 154(b) by 1312 days.

(21) Appl. No.: 10/946,435

(22) Filed: Sep. 21, 2004

(65) Prior Publication Data

US 2006/0060207 A1    Mar. 23, 2006

(51) Int. Cl.
*A61F 5/56*    (2006.01)
(52) U.S. Cl. .......... 128/848; 602/902
(58) Field of Classification Search .......... 128/846, 128/848, 897, 899; 601/15, 21, DIG. 3; 600/2, 9, 12, 15
See application file for complete search history.

(56) References Cited

U.S. PATENT DOCUMENTS

| | | | |
|---|---|---|---|
| 4,978,323 A | 12/1990 | Freedman | |
| 5,015,538 A | 5/1991 | Krause et al. | |
| 5,117,816 A | 6/1992 | Shapiro et al. | |
| 5,176,618 A | 1/1993 | Freedman | |
| 5,199,424 A | 4/1993 | Sullivan et al. | |
| 5,245,995 A | 9/1993 | Sullivan et al. | |
| 5,268,082 A | 12/1993 | Oguro et al. | |
| 5,284,161 A | 2/1994 | Karell | |
| 5,479,944 A | 1/1996 | Petruson | |
| 5,509,888 A | 4/1996 | Miller | |
| 5,520,849 A * | 5/1996 | Eiffler | 252/500 |
| 5,522,382 A | 6/1996 | Sullivan et al. | |
| 5,551,418 A | 9/1996 | Estes et al. | |
| 5,823,187 A | 10/1998 | Estes et al. | |
| 5,873,363 A | 2/1999 | Esmailzadeh | |
| RE36,120 E | 3/1999 | Karell | |
| 5,901,704 A | 5/1999 | Estes et al. | |
| 5,904,141 A | 5/1999 | Estes et al. | |
| 5,970,975 A | 10/1999 | Estes et al. | |
| 5,979,456 A | 11/1999 | Magovern | |
| 5,980,998 A | 11/1999 | Sharma et al. | |

(Continued)

FOREIGN PATENT DOCUMENTS

DE        4412190 A1    10/1995

(Continued)

OTHER PUBLICATIONS

U.S. Appl. No. 12/072,680, filed Feb. 27, 2008, Doelling et al.

(Continued)

*Primary Examiner*—Patricia M Bianco
*Assistant Examiner*—Keri J Nicholson
(74) *Attorney, Agent, or Firm*—Townsend and Townsend and Crew LLP

(57) ABSTRACT

A system and device for maintaining and/or creating patency in airways is disclosed. The methods of using the system and device are also disclosed. The system includes a power source that energizes a electro-active polymer implant. The energized polymer implant provides stiffness and shape to the airway, thereby minimizing collapse or deformation of the airway. A method of making the device is also disclosed.

59 Claims, 15 Drawing Sheets

U.S. PATENT DOCUMENTS

| | | | |
|---|---|---|---|
| 5,988,171 A | 11/1999 | Sohn et al. | |
| 6,048,383 A * | 4/2000 | Breault et al. | 95/44 |
| 6,092,523 A | 7/2000 | Belfer et al. | |
| 6,098,629 A | 8/2000 | Johnson et al. | |
| 6,109,852 A | 8/2000 | Shahinpoor et al. | |
| 6,124,965 A * | 9/2000 | Doi et al. | 359/248 |
| 6,190,893 B1 | 2/2001 | Shastri et al. | |
| 6,212,435 B1 | 4/2001 | Lattner et al. | |
| 6,250,307 B1 | 6/2001 | Conrad et al. | |
| 6,257,234 B1 | 7/2001 | Sun et al. | |
| 6,376,971 B1 | 4/2002 | Pelrine et al. | |
| 6,379,393 B1 | 4/2002 | Mavroidis et al. | |
| 6,390,096 B1 | 5/2002 | Conrad et al. | |
| 6,401,717 B1 | 6/2002 | Conrad et al. | |
| 6,408,851 B1 | 6/2002 | Karell | |
| 6,415,796 B1 | 7/2002 | Conrad et al. | |
| 6,431,174 B1 | 8/2002 | Knudson et al. | |
| 6,439,238 B1 | 8/2002 | Brenzel et al. | |
| 6,450,169 B1 | 9/2002 | Conrad et al. | |
| 6,453,905 B1 | 9/2002 | Conrad et al. | |
| 6,454,803 B1 | 9/2002 | Romo, III | |
| 6,467,485 B1 | 10/2002 | Schmidt et al. | |
| 6,475,639 B2 | 11/2002 | Shahinpoor et al. | |
| 6,502,574 B2 | 1/2003 | Stevens et al. | |
| 6,513,530 B2 | 2/2003 | Knudson et al. | |
| 6,513,531 B2 | 2/2003 | Knudson et al. | |
| 6,514,237 B1 | 2/2003 | Maseda | |
| 6,516,806 B2 | 2/2003 | Knudson et al. | |
| 6,523,541 B2 | 2/2003 | Knudson et al. | |
| 6,523,542 B2 | 2/2003 | Knudson et al. | |
| 6,523,543 B2 | 2/2003 | Conrad et al. | |
| 6,524,736 B1 * | 2/2003 | Sompalli et al. | 429/42 |
| 6,529,777 B1 | 3/2003 | Holmstrom et al. | |
| 6,540,860 B1 * | 4/2003 | Suzuki | 156/230 |
| 6,545,384 B1 | 4/2003 | Pelrine et al. | |
| 6,546,936 B2 | 4/2003 | Knudson et al. | |
| 6,569,654 B2 | 5/2003 | Shastri et al. | |
| 6,578,580 B2 | 6/2003 | Conrad et al. | |
| 6,583,533 B2 | 6/2003 | Pelrine et al. | |
| 6,586,859 B2 | 7/2003 | Kornbluh et al. | |
| 6,601,584 B2 | 8/2003 | Knudson et al. | |
| 6,601,585 B1 | 8/2003 | Conrad et al. | |
| 6,613,203 B1 * | 9/2003 | Hobson et al. | 204/296 |
| 6,618,627 B2 | 9/2003 | Lattner et al. | |
| 6,619,290 B1 | 9/2003 | Zacco et al. | |
| 6,626,181 B2 | 9/2003 | Knudson et al. | |
| 6,628,040 B2 | 9/2003 | Pelrine et al. | |
| 6,629,527 B1 | 10/2003 | Estes et al. | |
| 6,634,362 B2 | 10/2003 | Conrad et al. | |
| 6,636,767 B1 | 10/2003 | Knudson et al. | |
| 6,664,718 B2 | 12/2003 | Pelrine et al. | |
| 6,667,825 B2 | 12/2003 | Lu et al. | |
| 6,679,836 B2 | 1/2004 | Couvillon, Jr. | |
| 6,707,236 B2 | 3/2004 | Pelrine et al. | |
| 6,742,524 B2 | 6/2004 | Knudson et al. | |
| 6,748,951 B1 | 6/2004 | Schmidt | |
| 6,749,556 B2 | 6/2004 | Banik | |
| 6,768,246 B2 | 7/2004 | Pelrine et al. | |
| 6,770,027 B2 | 8/2004 | Banik et al. | |
| 6,781,284 B1 | 8/2004 | Pelrine et al. | |
| 6,812,624 B1 | 11/2004 | Pei et al. | |
| 6,835,173 B2 | 12/2004 | Couvillon, Jr. | |
| 6,955,172 B2 | 10/2005 | Nelson et al. | |
| 7,073,505 B2 | 7/2006 | Nelson et al. | |
| 7,188,627 B2 | 3/2007 | Nelson et al. | |
| 7,216,648 B2 | 5/2007 | Nelson et al. | |
| 7,360,542 B2 | 4/2008 | Nelson et al. | |
| 7,367,340 B2 | 5/2008 | Nelson et al. | |
| 2002/0173848 A1 | 11/2002 | Sachs et al. | |
| 2003/0015198 A1 | 1/2003 | Heeke et al. | |
| 2003/0113535 A1 * | 6/2003 | Sun et al. | 428/354 |
| 2003/0140930 A1 | 7/2003 | Knudson et al. | |
| 2003/0149445 A1 | 8/2003 | Knudson et al. | |
| 2003/0149488 A1 | 8/2003 | Metzger et al. | |
| 2003/0192556 A1 | 10/2003 | Conrad et al. | |
| 2003/0196669 A1 | 10/2003 | Conrad et al. | |
| 2003/0212306 A1 | 11/2003 | Banik | |
| 2003/0236531 A1 * | 12/2003 | Couvillon, Jr. | 606/113 |
| 2004/0016433 A1 | 1/2004 | Estes et al. | |
| 2004/0019368 A1 | 1/2004 | Lattner et al. | |
| 2004/0020497 A1 | 2/2004 | Knudson et al. | |
| 2004/0020498 A1 | 2/2004 | Knudson et al. | |
| 2004/0045555 A1 | 3/2004 | Nelson et al. | |
| 2004/0045556 A1 | 3/2004 | Nelson et al. | |
| 2004/0049102 A1 | 3/2004 | Nelson et al. | |
| 2004/0073272 A1 | 4/2004 | Knudson et al. | |
| 2004/0112390 A1 | 6/2004 | Brooks et al. | |
| 2004/0134491 A1 | 7/2004 | Pflueger et al. | |
| 2004/0139975 A1 | 7/2004 | Nelson et al. | |
| 2004/0149290 A1 | 8/2004 | Nelson et al. | |
| 2004/0172054 A1 | 9/2004 | Metzger et al. | |
| 2005/0004417 A1 | 1/2005 | Nelson et al. | |
| 2005/0115572 A1 | 6/2005 | Brooks et al. | |
| 2005/0121039 A1 | 6/2005 | Brooks et al. | |
| 2005/0159637 A9 | 7/2005 | Nelson et al. | |
| 2005/0199248 A1 | 9/2005 | Pflueger et al. | |
| 2005/0268919 A1 | 12/2005 | Knudson et al. | |
| 2005/0284485 A9 | 12/2005 | Nelson et al. | |
| 2007/0186936 A1 | 8/2007 | Nelson et al. | |
| 2008/0066764 A1 | 3/2008 | Paraschac et al. | |
| 2008/0066765 A1 | 3/2008 | Paraschac et al. | |
| 2008/0066766 A1 | 3/2008 | Paraschac et al. | |
| 2008/0066767 A1 | 3/2008 | Paraschac et al. | |

FOREIGN PATENT DOCUMENTS

| | | |
|---|---|---|
| EP | 0312368 B1 | 4/1989 |
| EP | 0743076 B1 | 11/1996 |
| EP | 1306104 A2 | 5/2003 |
| WO | WO 88/10108 A1 | 12/1988 |
| WO | WO 96/11653 A1 | 4/1996 |
| WO | WO 97/26039 A1 | 7/1997 |
| WO | WO 02/13738 A1 | 2/2002 |
| WO | WO03/030727 A | 4/2003 |
| WO | WO 03/041612 A2 | 5/2003 |
| WO | WO 03/065947 A1 | 8/2003 |
| WO | WO 03/107523 A | 12/2003 |
| WO | WO 2004/043288 A2 | 5/2004 |

OTHER PUBLICATIONS

Carley, David W. et al. 1997. Adenosine A1 Receptor Agonist GR79236 Suppresses Apnea During All Sleep Stages in the Rat. *Sleep*. 20 (12): 1093-8.

Degaspari, John. Hot Stuff: Advanced Materials are Moving Out of the Lab and into the Commercial World. Mechanical Engineering, Feature Article, p. 40; Dec. 2002. http://www.memagazine.org/backissues/dec02/features/hotstuff/hotstuff.html. 9 pages (accessed on Feb. 27, 2006).

Flageole, Helene et al. 1995. Diaphragmatic Pacing in Children with Congenial Central Alveolar Hypoventilation Syndrome. *Surgery*. 118 (1): 25-8.

Grisius, Richard J. 1991. Maxillofacial Prosthetics. *Current Opinion in Dentistry*. 1 (2): 155-9.

Hansen, Helle et al. 1992. Undine's Syndrom (Alveolaer Hypoventilation). *Ugeskr Laeger*. 154 (31): 2160-1 (in Danish w/ English Summary on p. 2161).

Ilbawi, Michel N. et al. 1981. Diaphragm Pacing in Infants and Children: Report of a Simplified Technique and Review of Experience. *The Annals of Thoracic Surgery*. 31 (1): 61-5.

Kane, P.M. et al. 1983. Alloplastic Implants of the Larynx. *Arch Otolaryngol*. 109: 648-52.

Maurer, Joachim T. et al. 2005. Palatal Implants for Primary Snoring: Short-Term Results of a New Minimally Invasive Surgical Technique. *Otolaryngology-Head and Neck Surgery*. 132 (1): 125-31.

Nasaw, Daniel. 2004. As Sufferers of Sleep Apnea Grow, A Less-Invasive Treatment Arises. http://www.mdhealthnotes.net/04-918_sleep_apnea.html (accessed on Feb. 27, 2006).

Nordgard, Stale et al. 2004. Palatal Implants: A New Method for the Treatment of Snoring. *Acta Otolaryngol.* 124 (8): 970-5.

Oguro, Keisuke. Preparation Procedure: Ion-Exchange Polymer Metal Composites (IPMC) Membranes. Osaka National Research Institute, AIST, Japan. http://ndeaa.jpl.nasa.gov/nasa-nde/lommas/eap/IPMC_PrepProcedure.htm (accessed Feb. 24, 2006).

Ouelette, Jennifer. Smart Fluids Move into the Marketplace: Magneto- and Electro-Rheological Fluids Find New Uses. The Industrial Physicist Magazine, vol. 9, Issue 6, p. 14, Dec. 2003/Jan. 2004. http://www.aip.org/tip/INPHF/vol-9/iss-6/p14.htm. 8 pages (accessed on Feb. 27, 2006).

Pavel, Frank et al. 1994. Contemporary Oral and Maxillofacial Surgery. *Journal of the California Dental Association.* 22 (4): 35-8, 40, 42-6.

Preis, Carsten et al. 2001. Removal of the Connector on the Laryngeal Mask Airway Provides a Useful Alternative to the Intubating Laryngeal Mask. *Canadian Journal of Anaesthesia.* 48 (6): 600-3.

Sanna, N. et al. 2004. Prolonged Asystolia in A Young Athlete: A Case of Sinus Arrest During REM Sleep. *International Journal of Sports Medicine.* 25 (6): 457-60.

Troyk, Philip R. 1999. Injectable Electronic Identification, Monitoring, and Stimulation Systems. *Annual Review of Biomedical Engineering.* 1: 177-209.

Villain, E. et al. 2000. Stimulation Cardiaque Dans Les Spasmes Du Sanglot De L'enfant [Cardiac Pacing in Children with Breath-Holding Spells]. *Archives Des Maladies Du Coeur Et Des Vaisseaux.* 93 (5): 547-52. (In French, w/ English Summary).

Hegde, Anant V. et al., U.S. Appl. No. 11/233,493 entitled "Airway Implant and Methods of Making and Using", filed Sep. 21, 2005.

Hegde, Anant V. et al., entitled "Airway Implant Sensors and Methods of Making and Using the Same", filed Feb. 15, 2006.

Nelson, Lionel M. et al. 2005. Magnetic Airway Implants for the Treatment of Obstructive Sleep Apnea Syndrome. *Otolaryngology—Head and Neck Surgery Clinic.* 133 (6): 954-960. (Abstract Only).

Moore, et al.; "The use of a metal detector for lacalisation of a metallic foreign body in the floor of the mouth;" Jun. 1993; British Journal of Oral and Maxillofacial Surgery,; vol. 31, No. 3; pp. 191-192.

\* cited by examiner

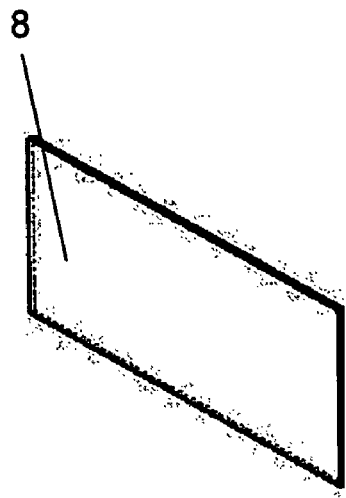
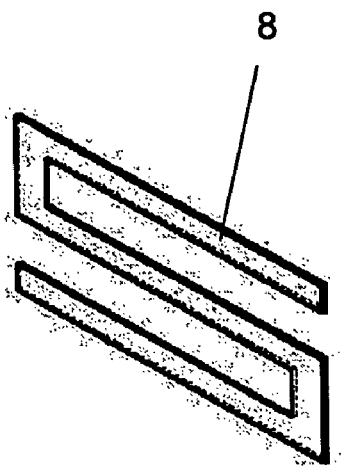
Fig. 9　　　　　Fig. 10
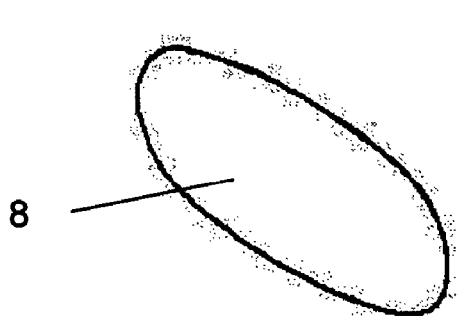
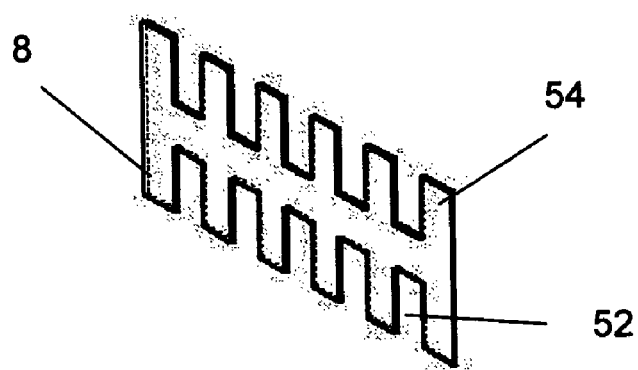
Fig. 11　　　　　Fig. 12

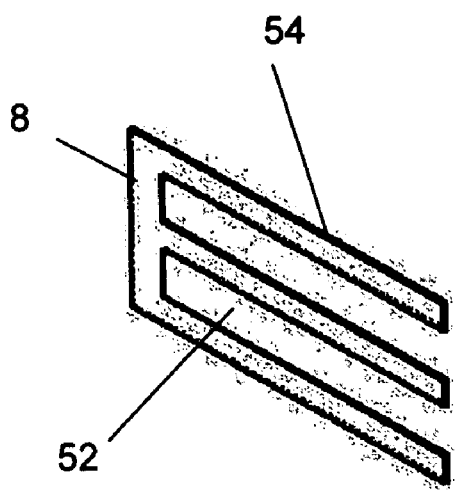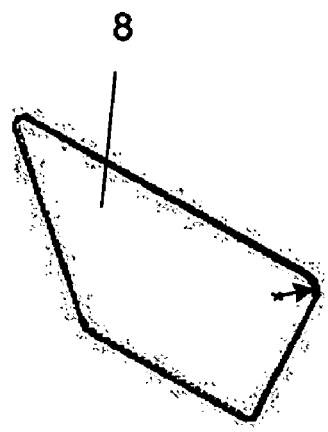
Fig. 13               Fig. 14
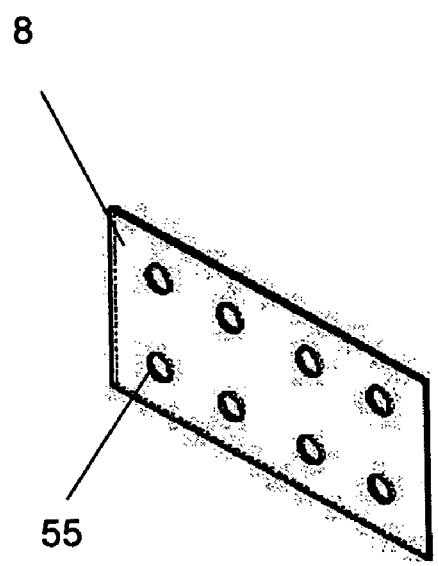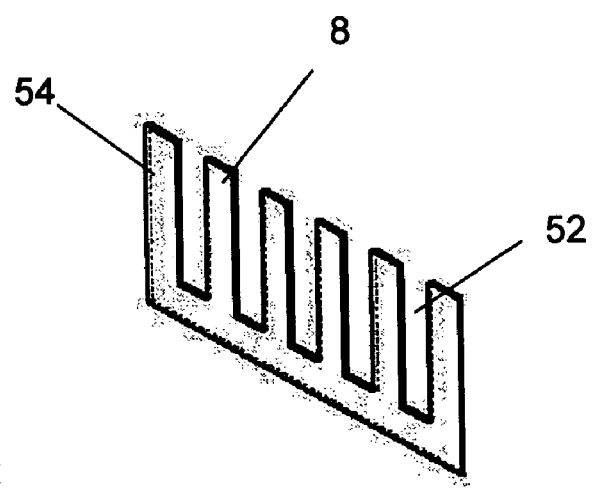
Fig. 15               Fig. 16

AIRWAY IMPLANT AND METHODS OF MAKING AND USING

BACKGROUND OF THE INVENTION

1. Field of the Invention

The invention relates to the systems, devices and methods for creating and/or maintaining airway patency, for example, for treating snoring and/or sleep apnea.

2. Description of the Related Art

Snoring is very common among mammals including humans. Snoring is a noise produced while breathing during sleep causes vibration of the soft palate and uvula. Not all snoring is bad, except it bothers the bed partner or others near the person who is snoring. If the snoring gets worst overtime and goes untreated, it could lead to apnea.

Those with apnea stop breathing in their sleep, often hundreds of times during the night. Usually apnea occurs when the throat muscles and tongue relax during sleep and partially block the opening of the airway. When the muscles of the soft palate at the base of the tongue and the uvula relax and sag, the airway becomes blocked, making breathing labored and noisy and even stopping it altogether. Sleep apnea also can occur in obese people when an excess amount of tissue in the airway causes it to be narrowed.

In a given night, the number of involuntary breathing pauses or "apneic events" may be as high as 20 to 60 or more per hour. These breathing pauses are almost always accompanied by snoring between apnea episodes. Sleep apnea can also be characterized by choking sensations.

Sleep apnea is diagnosed and treated by primary care physician, pulmonologists, neurologists, or other physicians with specialty training in sleep disorders. Diagnosis of sleep apnea is not simple because there can be many different reasons for disturbed sleep.

The specific therapy for sleep apnea is tailored to the individual patient based on medical history, physical examination, and the results of polysomnography. Medications are generally not effective in the treatment of sleep apnea. Oxygen is sometimes used in patients with central apnea caused by heart failure. It is not used to treat obstructive sleep apnea.

Nasal continuous positive airway pressure (CPAP) is the most common treatment for sleep apnea. In this procedure, the patient wears a mask over the nose during sleep, and pressure from an air blower forces air through the nasal passages. The air pressure is adjusted so that it is just enough to prevent the throat from collapsing during sleep. The pressure is constant and continuous. Nasal CPAP prevents airway closure while in use, but apnea episodes return when CPAP is stopped or it is used improperly. Many variations of the CPAP devices are available and all have the same side effects such as nasal irritation and drying, facial skin irritation, abdominal bloating, mask leaks, sore eyes, and headaches. Some versions of CPAP vary the pressure to coincide with the person's breathing pattern, and other CPAPs start with low pressure, slowly increasing it to allow the person to fall asleep before the full prescribed pressure is applied.

Dental appliances that reposition the lower jaw and the tongue have been helpful to some patients with mild to moderate sleep apnea or who snore but do not have apnea. A dentist or orthodontist is often the one to fit the patient with such a device.

Some patients with sleep apnea may need surgery. Although several surgical procedures are used to increase the size of the airway, none of them is completely successful or without risks. More than one procedure may need to be tried before the patient realizes any benefits. Some of the more common procedures include removal of adenoids and tonsils (especially in children), nasal polyps or other growths, or other tissue in the airway and correction of structural deformities. Younger patients seem to benefit from these surgical procedures more than older patients.

Uvulopalatopharyngoplasty (UPPP) is a procedure used to remove excess tissue at the back of the throat (tonsils, uvula, and part of the soft palate). The success of this technique may range from 30 to 60 percent. The long-term side effects and benefits are not known, and it is difficult to predict which patients will do well with this procedure.

Laser-assisted uvulopalatoplasty (LAUP) is done to eliminate snoring but has not been shown to be effective in treating sleep apnea. This procedure involves using a laser device to eliminate tissue in the back of the throat. Like UPPP, LAUP may decrease or eliminate snoring but not eliminate sleep apnea itself. Elimination of snoring, the primary symptom of sleep apnea, without influencing the condition may carry the risk of delaying the diagnosis and possible treatment of sleep apnea in patients who elect to have LAUP. To identify possible underlying sleep apnea, sleep studies are usually required before LAUP is performed.

Somnoplasty is a procedure that uses RF to reduce the size of some airway structures such as the uvula and the back of the tongue. This technique helps in reducing snoring and is being investigated as a treatment for apnea.

Tracheostomy is used in persons with severe, life-threatening sleep apnea. In this procedure, a small hole is made in the windpipe and a tube is inserted into the opening. This tube stays closed during waking hours and the person breathes and speaks normally. It is opened for sleep so that air flows directly into the lungs, bypassing any upper airway obstruction. Although this procedure is highly effective, it is an extreme measure that is rarely used.

Patients in whom sleep apnea is due to deformities of the lower jaw may benefit from surgical reconstruction. Surgical procedures to treat obesity are sometimes recommended for sleep apnea patients who are morbidly obese. Behavioral changes are an important part of the treatment program, and in mild cases behavioral therapy may be all that is needed. Overweight persons can benefit from losing weight. Even a 10 percent weight loss can reduce the number of apneic events for most patients. Individuals with apnea should avoid the use of alcohol and sleeping pills, which make the airway more likely to collapse during sleep and prolong the apneic periods. In some patients with mild sleep apnea, breathing pauses occur only when they sleep on their backs. In such cases, using pillows and other devices that help them sleep in a side position may be helpful.

Recently, company—Restore Medical, Inc., Saint Paul, Minn. has developed a new treatment for snoring and apnea and the technique is called Pillar™ technique. Pillar™ System is a minimally invasive procedure where 2 or 3 small polyester rod type devices are placed in patient's soft palate. The Pillar™ System stiffens the palate and reduces the vibration of the tissue and prevents the possible airway collapse. Stiff implants in the soft palate could hinder patient's normal functions like speech, ability to swallow, coughing and sneezing. Protrusion in the airway is another long-term concern.

BRIEF SUMMARY OF THE INVENTION

A new type of implant to treat patients with snoring and/or apnea is disclosed. An electroactive polymeric (EAP) device can be inserted in the soft palate and/or sidewalls of the patient's airway. The polymeric implant can have a very low stiffness under normal conditions. When the polymeric device is energized, the polymer can become stiff and tend to deform. The polymeric device, in its energized state, can have the ability to support the weight of the soft palate and sidewalls of the patient. When the charge is removed, the polymeric device can become soft and not interfere with the patient's normal activities like swallowing and speech.

Electroactive polymer (EAP) is a type of polymer that can respond to electrical stimulation by physical deformation, change in tensile properties and change in hardness. There are several types of electroactive polymers like dielectric electrostrictive polymer, ion exchange polymer and ion exchange polymer metal composite (IPMC). The particular type of EAP used in the making of the disclosed device can be any of the aforementioned electroactive polymers, such as IPMC.

IPMC is a polymer and metal composite that uses an ionomer as the base material. Ionomers are types of polymers that allow for ion movement through the membrane. There are several ionomers available in the market and some of the suited ionomers for this application are polyethylene, polystyrene, polytetrafluoroethylene, polyvinylidene fluoride, polyfluorosulfonic acid based membranes like NAFION® (from E.I. Du Pont de Nemours and Company, Wilmington, Del.), polyaniline, polyacrylonitrile, cellulose, cellulose acetates, regenerated cellulose, polysulfone, polyurethane, or combinations thereof. A conductive metal, for example gold, silver, platinum, palladium, copper, carbon, or combinations thereof, can be deposited on the ionomer to make the IPMC.

The IPMC element can be formed in many shapes, for example, a strip, rod, cylindrical tube, rectangular piece, triangular piece, trapezoidal shape, arch shapes, coil shapes, or combinations thereof. The IPMC element can have perforations or slots cut in them to allow tissue in growth.

One or more implants can be placed in the soft palate, sidewalls of the airway, around the trachea, in the tongue, in the uvula, or in combinations thereof. The implant can have lead wires (e.g., anode and cathode) attached to the surfaces. The lead wires can be connected to an induction coil. The induction coil can be implanted in the roof of the mouth. The patient can wear a specially fitted retainer type of device before going to bed every night. The retainer can have an induction coil, a circuit and a battery. When the patient wears the retainer, the induction coil in the retainer is aligned with the induction coil that is implanted in the roof of the mouth. The energy can be transmitted through the tissue and to the coil that is in the roof of the mouth. The IPMC implant can be energized, deform and stiffen to provide support. Patient can relax and sleep without the worry of the airway collapse in their sleep. In the morning when the patient wakes up, the patient can remove the retainer and place the retainer on a charging unit to recharge the battery.

BRIEF DESCRIPTION OF THE DRAWINGS

FIGS. 9 through 19 illustrate perspective views of various embodiments of the patency element.

DETAILED DESCRIPTION

Figure 1:
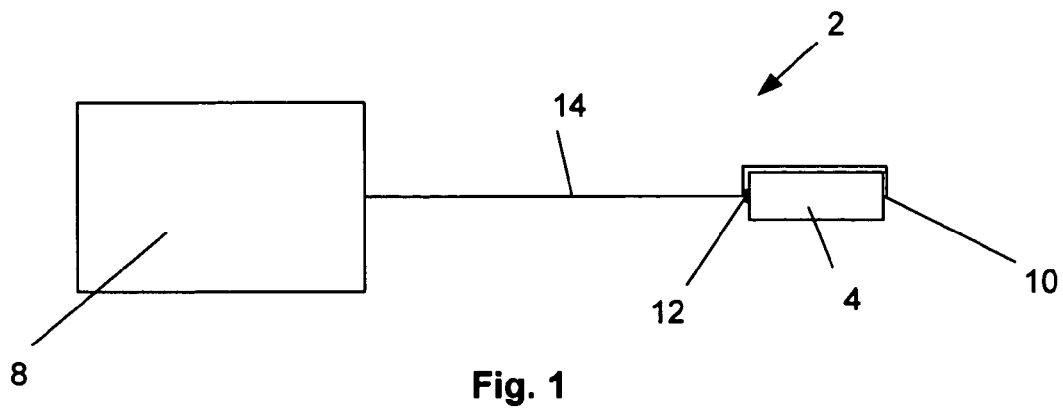
FIGS. 1 through 3 illustrate various embodiments of the patency system.

FIG. 1 illustrates an electro-active patency system 2 that can have a power supply 4, a connecting element, such as a wire lead 6, and a patency element 8 that can be made from an electro-active polymer.

The power supply 4 can be a power cell, a battery, a capacitor, a substantially infinite bus (e.g., a wall outlet leading to a power generator), a generator (e.g., a portable generator, a solar generator, an internal combustion generator), or combinations thereof. The power supply 4 can have a power output of from about 1 mA to about 5 A, for example about 500 mA.

The connecting element can be the wire lead 6, an inductive energy transfer system, a conductive energy transfer system, a chemical energy transfer system, an acoustic or otherwise vibratory energy transfer system, a nerve or nerve pathway, other biological tissue, or combinations thereof. The connecting element can be made from one or more conductive materials, such as copper. The connecting element can be completely or partially insulated and or protected by an insulator, for example polytetrafluoroethylene (PTFE). The insulator can be biocompatible. The power supply 4 can be in electrical communication with the patency element 8 through the connecting element. The connecting element can be attached to an anode 10 and a cathode 12 on the power supply 4. The connecting element can be made from one or more sub-elements.

The patency element 8 can be made from an electro-active polymer. The electro-active polymer can have an ion exchange polymer metal composite (IPMC). The IPMC can have a base polymer embedded, or otherwise appropriately mixed, with a metal. The IPMC base polymer can be perfluoronated polymer, polytetrafluoroethylene, polyfluorosulfonic acid, perfluorosulfonate, polyvinylidene fluoride, hydrophilic polyvinylidene fluoride, polyethylene, polypropylene, polystyrene, polyaniline, polyacrylonitrile, cellophane, cellulose, regenerated cellulose, cellulose acetate, polysulfone, polyurethane, polyvinyl alcohol, polyvinyl acetate and polyvinyl pyrrolidone, or combinations thereof. The IPMC metal can be platinum, gold, silver, palladium, copper, carbon, or combinations thereof.

Figure 2:
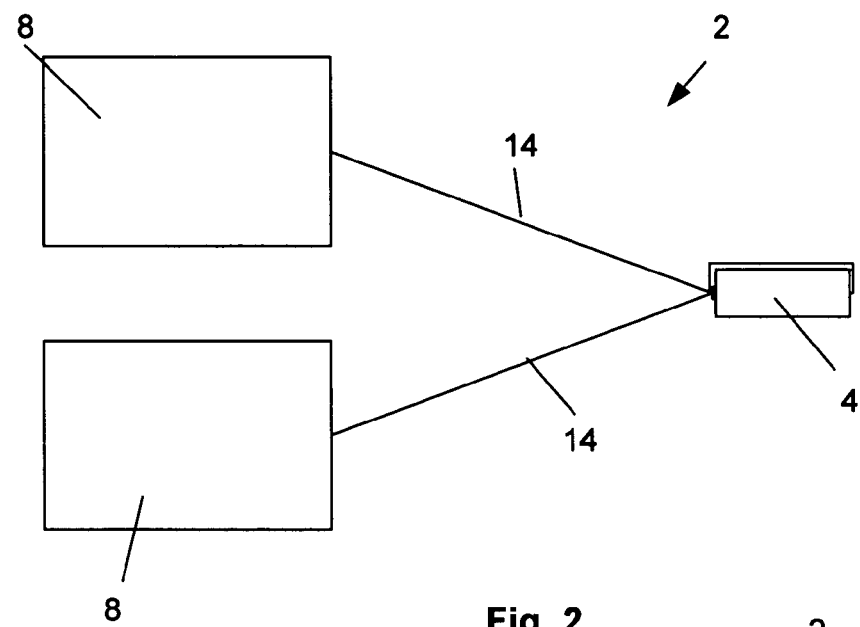

FIG. 2 illustrates that the patency system 2 can have multiple patency elements 8 and connecting elements 14 that can all connect to a single power supply 4.

Figure 3:
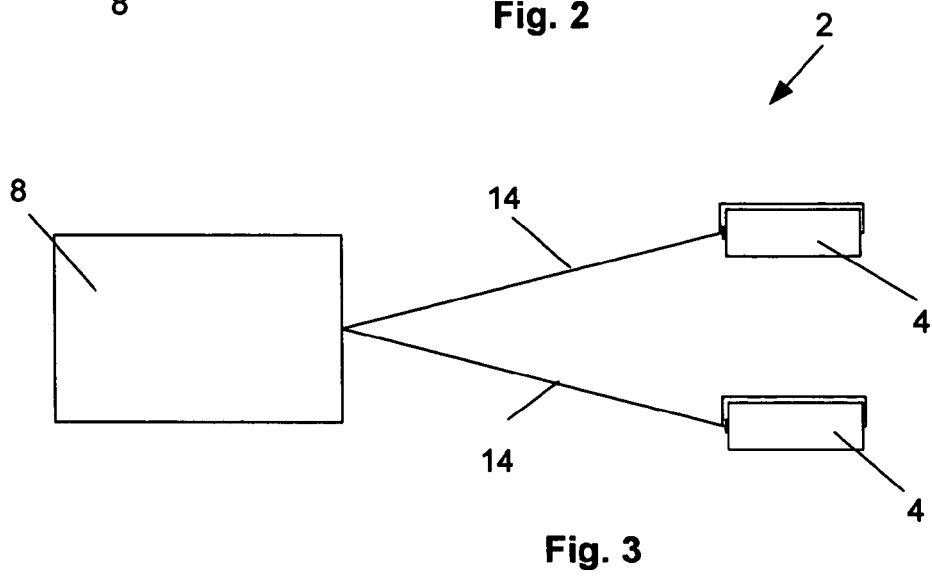

FIG. 3 illustrates that the patency system 2 can have multiple power supplies 4 and connecting elements 14 that can all connect to a single patency element 8. The patency system 2 can have any number and combination of patency elements 8 connected to power supplies 4.

Figure 4:
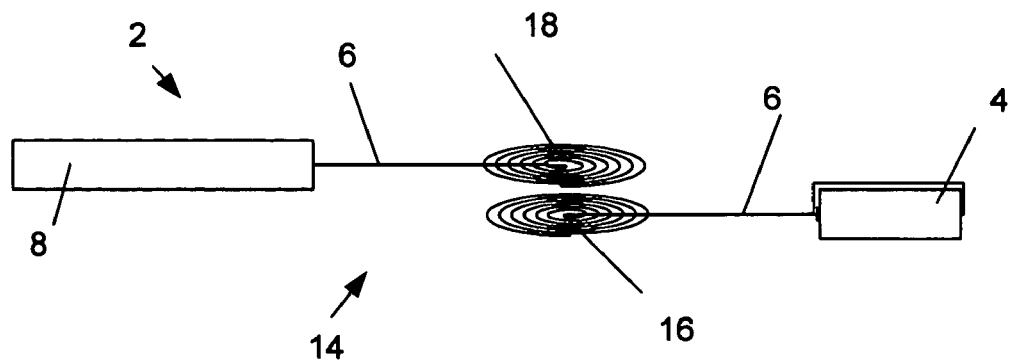
FIG. 4 illustrates an embodiment of the patency system.

FIG. 4 illustrates that the connecting element can have a first energy transfer element, for example a first transducer such as a first receiver, and a second energy transfer element, for example a second transducer such as a second inductor 16. The first receiver can be a first inductor 18. The first inductor 18 can be positioned close enough to the second inductor 16 to enable sufficient inductive electricity transfer between the second and first inductors 16 and 18 to energize the patency element 8.

Figure 5:
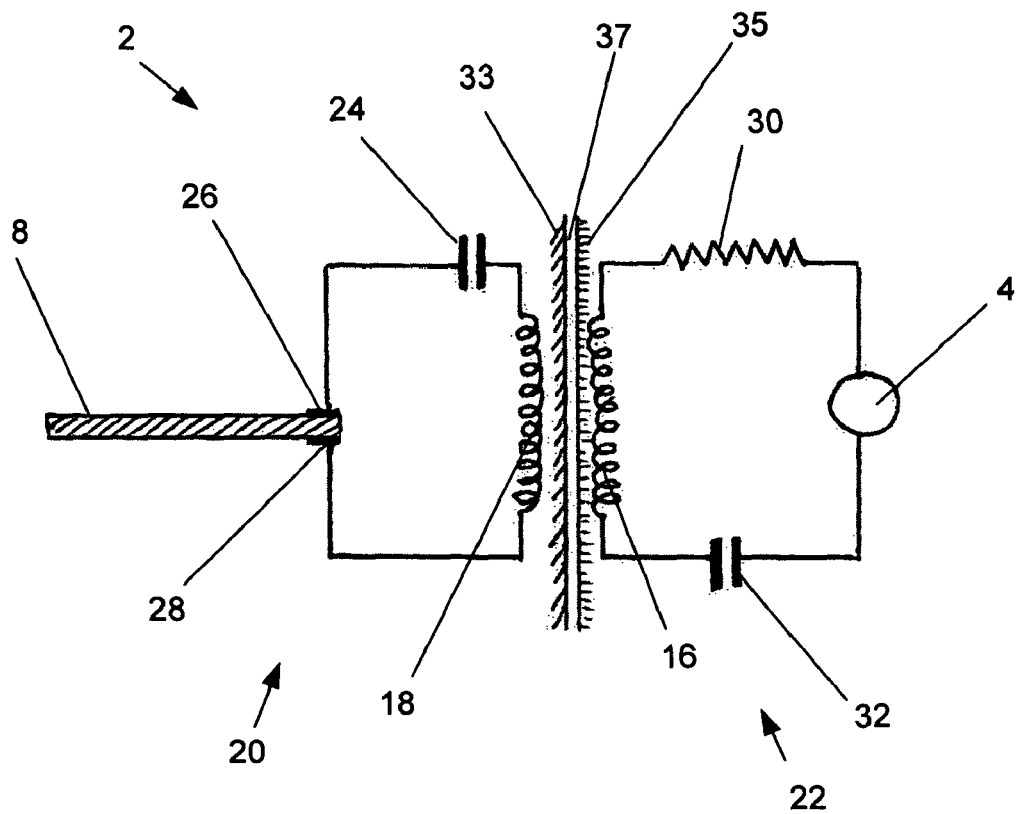
FIG. 5 illustrates a circuit diagram of an embodiment of the patency system in use.

FIG. 5 illustrates that the patency system of FIG. 4 can have an implanted portion 20 and a non-implanted portion 22. The implanted portion 20 can be a closed circuit with the first inductor 18 in series with a first capacitor 24 and the patency element 8. The patency element 8 can be attached to the closed circuit of the implanted portion 20 by a first contact 26 and a second contact 28. The implanted portion can have a resistor (not shown).

The non-implanted portion 22 can be a closed circuit. The non-implanted portion 22 can have a second inductor 16 that can be in series with a resistor 30, the power supply 4, and a second capacitor 32. The capacitors, resistors, and, in-part, the inductors can be representative of the electrical characteristics of the wire of the circuit and not necessarily representative of specific elements.

The implanted portion 20 can be within tissue and have a tissue surface 33 nearby. The non-implanted portion can be in insulation material 35. An air interface 37 can be between the tissue surface 33 and the insulation material 35.

Figure 6:
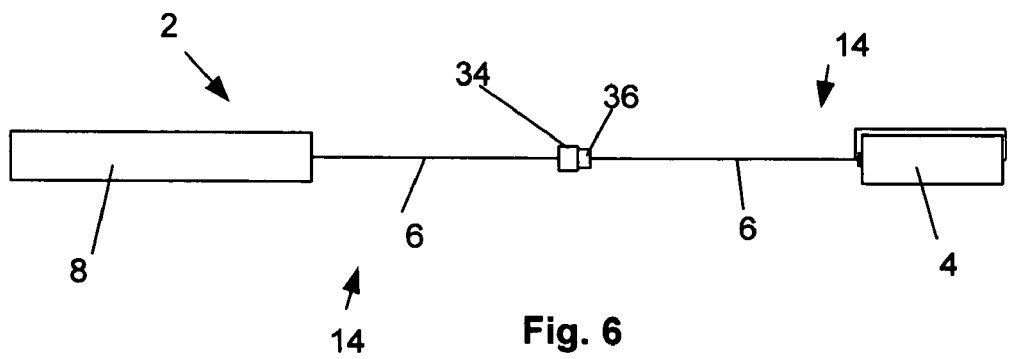
FIG. 6 illustrates an embodiment of the patency system.

FIG. 6 illustrates that the first energy transfer element of the connecting element 14 can be a first conductor 34. The second energy transfer element of the connecting element 14 can be a second conductor 36. The first conductor 34 can be configured to plug into, receive, or otherwise make secure electrical conductive contact with the second conductor 36. The first conductor 34 and/or second conductor 36 can be plugs, sockets, conductive dental fillings, tooth caps, fake teeth, or any combination thereof.

Figure 7:
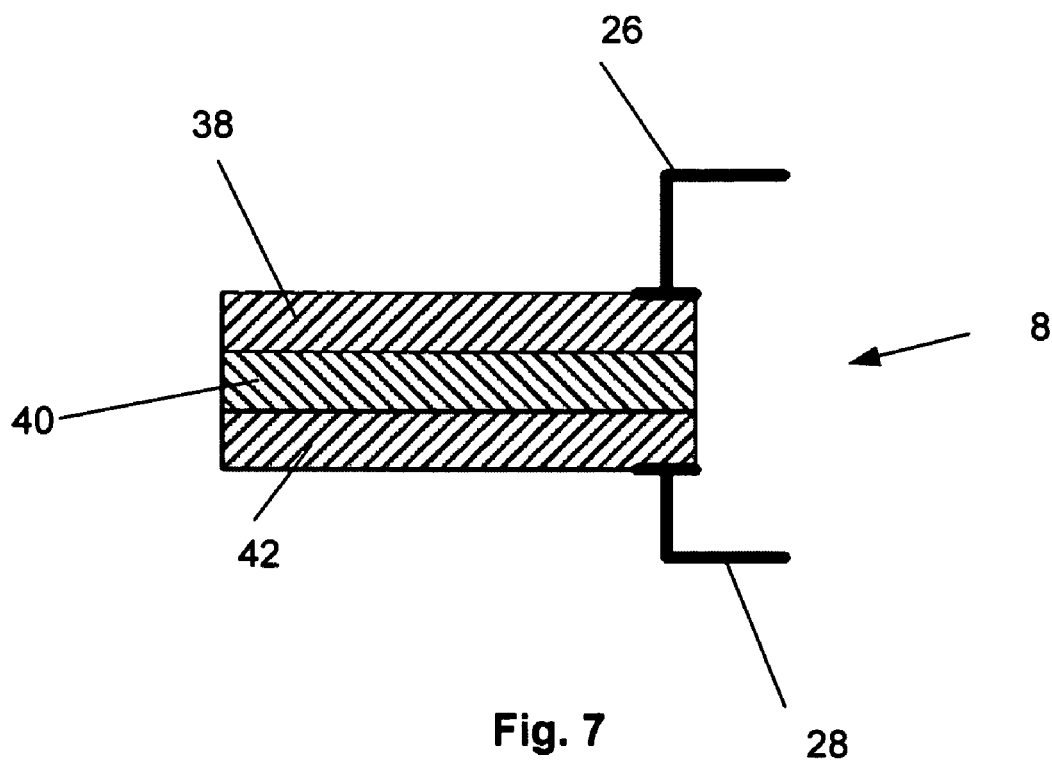
FIGS. 7 and 8 illustrate various sectional views of the patency element.

FIG. 7 illustrates that the patency element 8 can be a multi-layered device. The patency element 8 can have a first EAP layer 38, a second EAP layer 40, and a third EAP layer 42. The EAP layers 38, 40 and 42 can be in contact with each other and not separated by an insulator.

Figure 8:
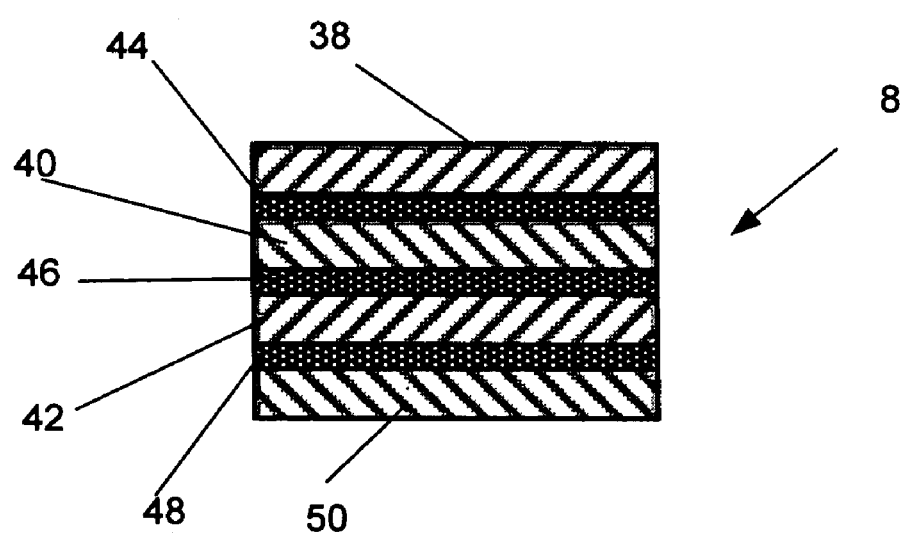

FIG. 8 illustrates that the patency element 8 can have a first EAP layer 38 separated from a second EAP layer 40 by a first insulation layer 44. A second insulation layer 46 can separate the second EAP layer from the third EAP layer 42. A third insulation layer 48 can separate the third EAP layer from the fourth EAP layer 50. Insulation material can be a polymeric material that electrically isolates each layer. The insulation can be, for example, acrylic polymers, polyimide, polypropylene, polyethylene, silicones, nylons, polyesters, polyurethanes, or combinations thereof. Each EAP layer, 38, 40, 42 and 50 can be connected to a lead wire (not shown). All anodes and all cathodes can be connected to the power supply 4.

FIG. 9 illustrates that the patency element 8 can have a substantially flat rectangular configuration. The patency element 8 can have a width from about 2 mm to about 5 cm, for example about 1 cm. FIG. 10 illustrates that the patency element 8 can have an "S" or zig-zag shape. FIG. 11 illustrates that the patency element 8 can have an oval shape. FIG. 12 illustrates that the patency element 8 can have a substantially flat rectangular shape with slots 52 cut perpendicular to the longitudinal axis of the patency element 8. The slots 52 can originate near the longitudinal axis of the patency element 8. The patency element 8 can have legs 54 extending away from the longitudinal axis.

FIG. 13 illustrates that the patency element 8 can have slots 52 and legs 54 parallel with the longitudinal axis. FIG. 14 illustrates that the patency element can be configured as a quadrilateral, such as a trapezoid. The patency element 8 can have chamfered corners, as shown by radius. FIG. 15 illustrates that the patency element 8 can have apertures 55, holes, perforations, or combinations thereof. FIG. 16 illustrates that the patency element 8 can have slots 52 and legs 54 extending from a side of the patency element 8 parallel with the longitudinal axis.

Figure 17:
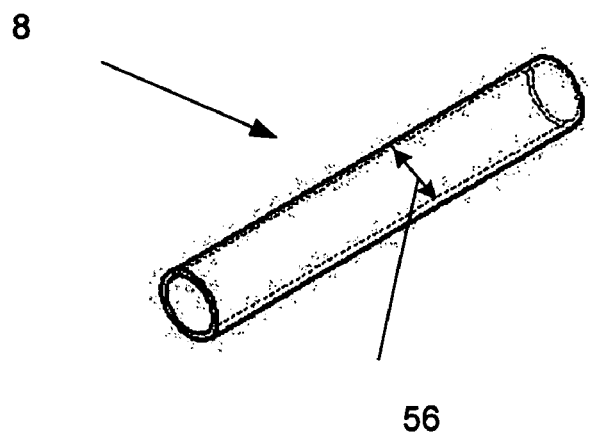

FIG. 17 illustrates that the patency element 8 can be a hollow cylinder, tube or rod. The patency element can have an inner diameter 56.

Figure 18:
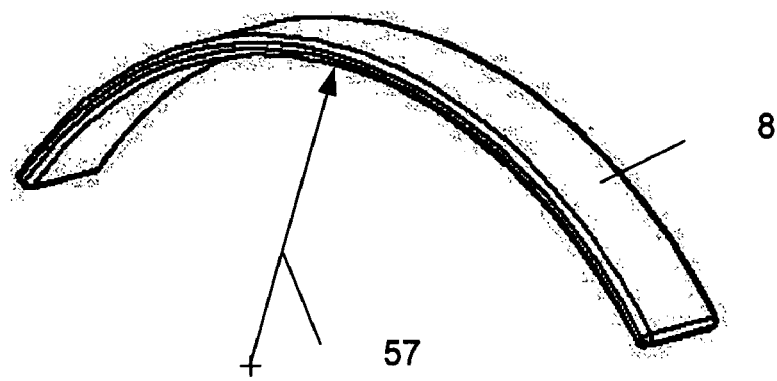

FIG. 18 illustrates an arched patency element 8. The arch can have a radius of curvature 57 from about 1 cm to about 10 cm, for example about 4 cm. The patency element 8 can have a uniform thickness.

Figure 19:
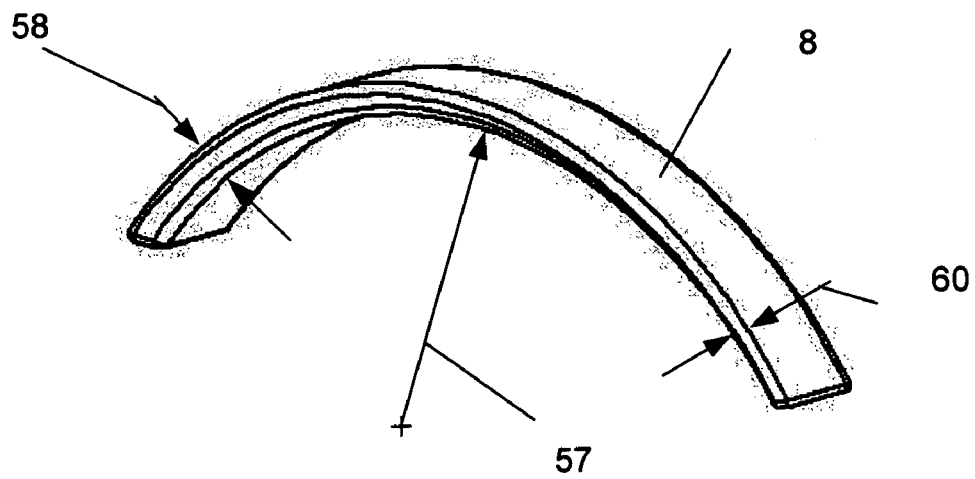

FIG. 19 illustrates an arched patency element 8. The patency element 8 can have a varying thickness. A first thickness 58 can be equal or greater than a second thickness 60.

Figure 20:
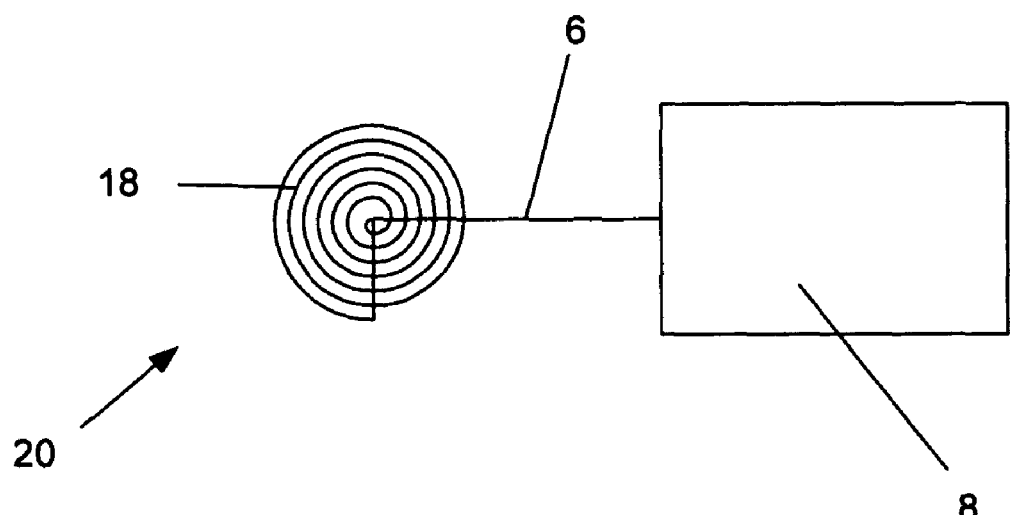
FIGS. 20 and 21 illustrate various embodiments of the implanted portion of the patency system.

FIG. 20 illustrates that the implanted portion can have a coil-type inductor 18 connected by the wire lead 6 to the patency element 8.

Figure 21:
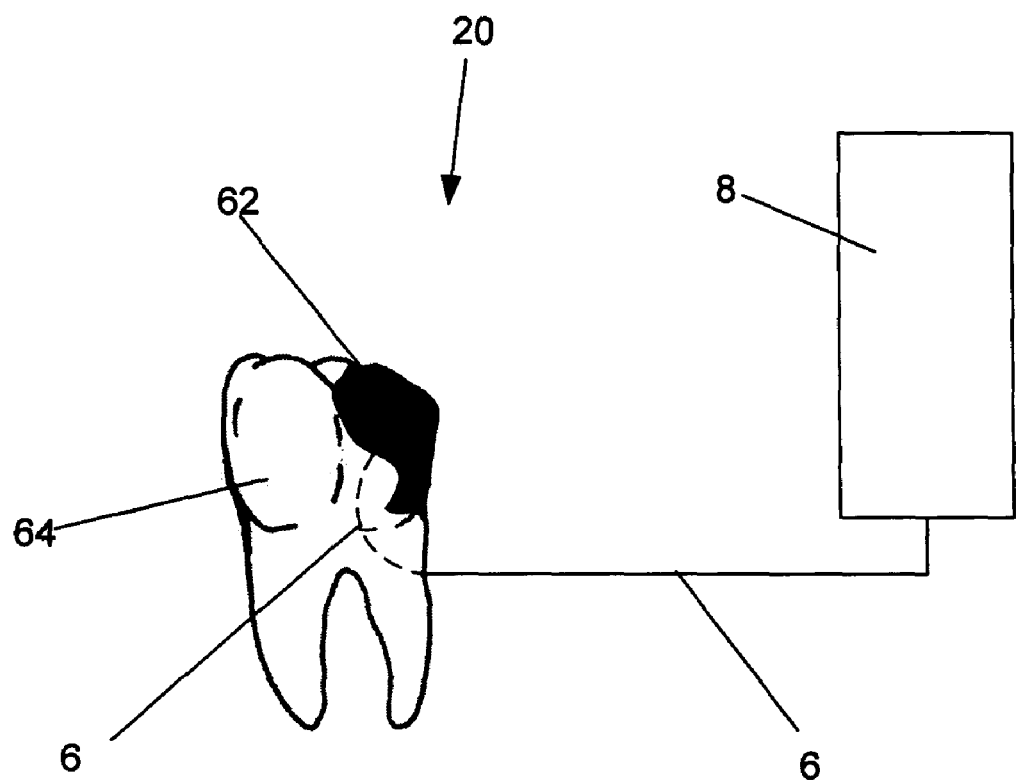

FIG. 21 illustrates that the implanted portion can have a conductive dental filling 62 in a tooth 64. The dental filling 62 can be previously implanted for reasons related or unrelated to airway patency. The dental filling 62 can be electrically connected to the wire lead 6. For example, the a portion of the wire lead 6 can be implanted in the tooth 64, as shown by phantom line. The wire lead 6 can be connected to the patency element 8.

Figure 22:
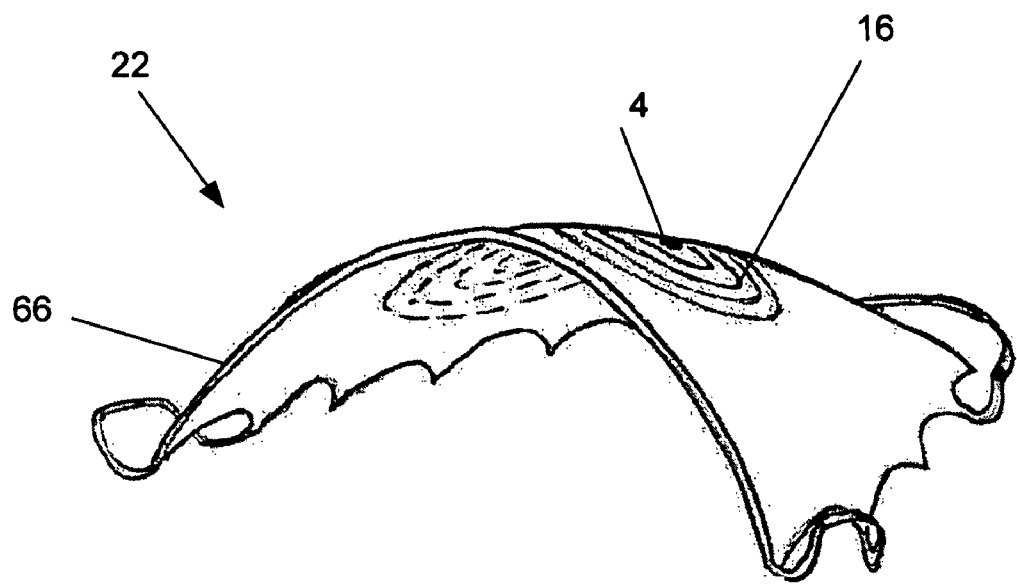
FIGS. 22 through 24 illustrate various embodiments of the second transducers.

FIG. 22 illustrates that the non-implanted portion 22 can have a mouthpiece, such as a retainer 66. The retainer 66 can be custom configured to fit to the patient's mouth roof, or another part of the patient's mouth. The second transducer, such as second inductor 16, can be integral with, or attached to, the retainer 66. The second inductor 16 can be located in the retainer 66 so that during use the second inductor 16 can be substantially aligned with the first inductor 18. The power supply 4, such as a cell, can be integral with, or attached to, the retainer 66. The power supply 4 can be in electrical communication with the second inductor 16. The retainer 66 can have a pulse-width-modulation circuit.

Figure 23:
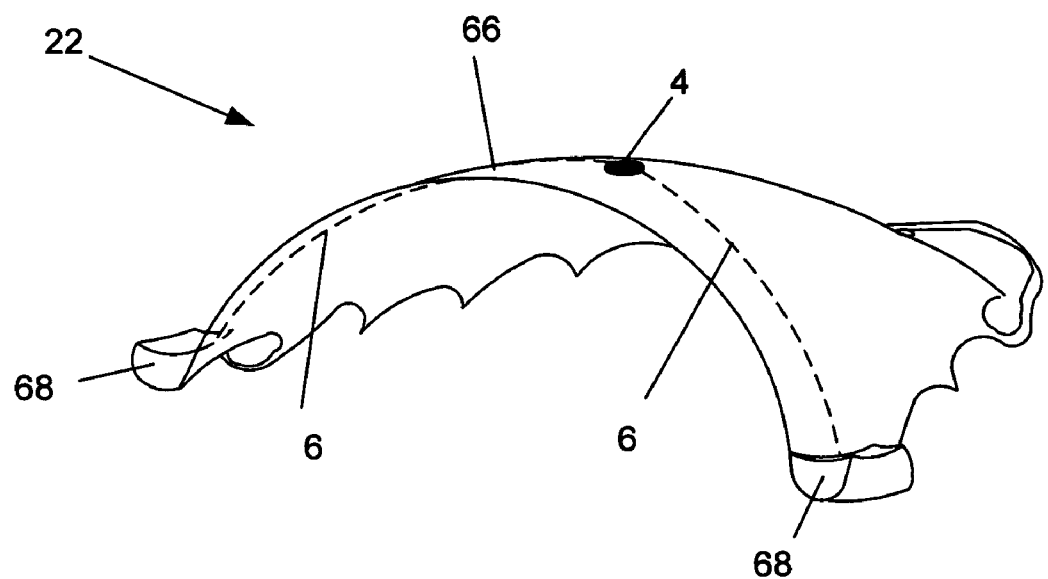

FIG. 23 illustrates that the retainer 66 can have one or more tooth sockets 68. The tooth sockets 68 can be configured to receive teeth that have dental fillings. The tooth sockets 68 can be electrically conductive in areas where they align with dental fillings when in use. The power supply 4 can be connected with the tooth sockets 68 via the wire leads 6.

Figure 24:
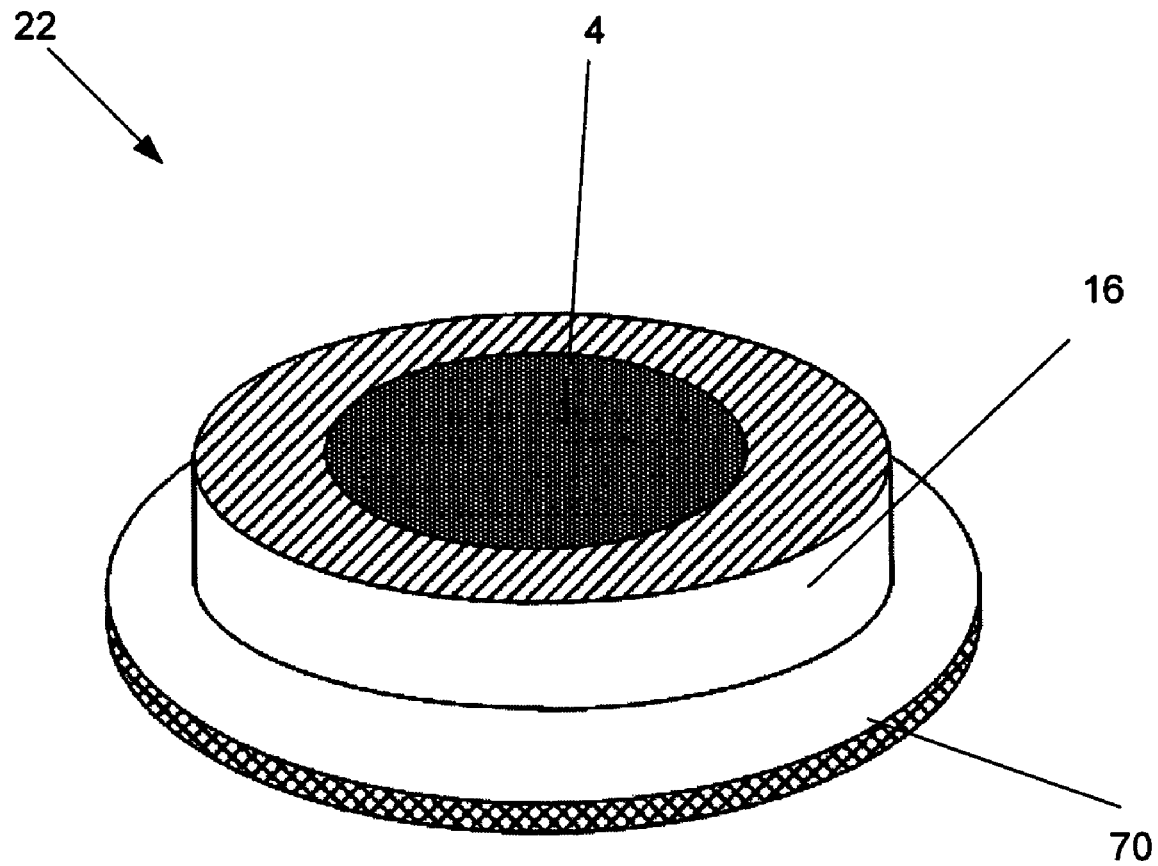

FIG. 24 illustrates that the non-implantable portion 22 can have the second inductor 16 attached to a removably attachable patch 70. The patch 70 can be attached to the power supply 4. The power supply 4 can be in contact with the second inductor 16.

Method of Making

The patency element 8, for example an IPMC strip, can be made from a base material of an ionomer sheet, film or membrane. The ionomer sheet can be formed using ionomer dispersion.

IPMC can be made from the base ionomer of, for example, polyethylene, polystyrene, polytetrafluoroethylene, polyvinylidene fluoride (PVDF) (e.g., KYNAR® and KYNAR Flex®, from ATOFINA, Paris, France, and SOLEF®, from Solvay Solexis S.A., Brussels, Belgium), hydrophilic-PVDF (h-PVDF), polyfluorosulfonic acid based membranes like NAFION® (from E.I. Du Pont de Nemours and Company, Wilmington, Del.), polyaniline, polyacrylonitrile, cellulose, cellulose acetates, regenerated cellulose, polysulfone, polyurethane, and combinations thereof. The conductive material that is deposited on the ionomer can be gold, platinum, silver, palladium, copper, graphite, conductive carbon, or combinations thereof. Conductive material can be deposited on the ionomer either by electrolysis process, vapor deposition, sputtering, electroplating, or combination of processes.

The IPMC can be cut into the desired implant shape, such as those shown in FIGS. 9 through 19. The wire leads 6 (e.g., anode and cathode wires for each patency element) can be connected to the IPMC surfaces by, for example, soldering, welding, brazing, potting using conductive adhesives, or combinations thereof. The patency element 8 can be configured into specific curved shapes using mold and heat setting processes.

The patency element 8 can be insulated with electrical insulation coatings. The patency element 8 can be insulated with coatings that promote cell growth and minimize fibrosis, stop cell growth, or kill nearby cells. The patency element 8 can be insulated with a biocompatible material. The patency element 8 can be coated with polymers such as polypropylene, poly-L-lysine, poly-D-lysine, polyethylene glycol, povinyl alcohol, polyvinyl acetate, polymethyl methacrylate, or combinations thereof. The patency element can be coated with hyaluronic acid. The coating can be applied to the device by standard coating techniques like spraying, electrostatic spraying, brushing, vapor deposition, dipping, etc.

In one example, a perfluorosulfonate ionomer, PVDF or h-PVDF sheet can be prepared for manufacturing the patency element 8. The sheet can be roughened on both sides using, for example, about 320 grit sand paper and then about 600 grit sand paper. The sheet can then be rinsed with deionized water. The sheet can then be submerged in isopropyl alcohol (IPA), and subjected to an ultrasonic bath for about 10 minutes. The sheet can then be rinsed with deionized water. The sheet can then be boiled for about 30 minutes in hydrochloric acid (HCL). The sheet can then be rinsed and then boiled in deionized water for about 30 minutes.

The sheet can then be subject to ion-exchange (i.e., absorption). The sheet can be submerged into, or otherwise exposed to, a metal salt solution at room temperature for more than about three hours. Examples of the metal salt solution are tetraammineplatinum chloride solution, silver chloride solution, hydrogen tetrachloroaurate, tetraamminepalladium chloride monohydrate or other platinum, gold, silver, carbon, copper, or palladium salts in solution. The metal salt solution can have a concentration of greater than or equal to about 200 mg/100 ml water. 5% ammonium hydroxide solution can be added at a ratio of 2.5 ml/100 ml to the tetraammineplatinum chloride solution to neutralize the solution. The sheet can then be rinsed with deionized water.

A primary plating can then be applied to the sheet. The sheet can be submerged in water at about 40° C. A 5% solution by weight of sodium borohydride and deionized water can be added to the water submerging the sheet at 2 ml/180 ml of water. The solution can stir for 30 minutes at 40° C. The sodium borohydride solution can then be added to the water at 2 ml/180 ml of water and the solution can stir for 30 minutes at 40° C. This sodium borohydride adding and solution stirring can be performed six times total. The water temperature can then be gradually raised to 60° C. 20 ml of the sodium borohydride solution can then be added to the water. The solution can stir for about 90 minutes. The sheet can then be rinsed with deionized water, submerged into 0.1N HCl for an hour, and then rinsed with deionized water.

The sheet can then receive a second plating. The sheet can be submerged or otherwise exposed to a tetraammineplatinum chloride solution at a concentration of about 50 mg/100 ml deionized water. 5% ammonium hydroxide solution can be added at a rate of 2 ml/100 ml of tetraammineplatinum chloride solution. 5% by volume solution of hydroxylamine hydrochloride in deionized water can be added to the tetraammineplatinum chloride solution at a ratio of 0.1 of the volume of the tetraammineplatinum chloride solution. 20% by volume solution of hydrazine monohydrate in deionized water can be added to the tetraammineplatinum chloride solution at a ratio of 0.05 of the volume of the tetraammineplatinum chloride solution. The temperature can then be set to about 40° C. and the solution can be stirred.

A 5% solution of hydroxylamine hydrochloride can then be added at a ratio of 2.5 ml/100 ml of tetraammineplatinum chloride solution. A 20% solution of hydrazine monohydrate solution can then be added at a ratio of 1.25 ml/100 ml tetraammineplatinum chloride solution. The solution can be stirred for 30 minutes and the temperature set to 60° C. The above steps in this paragraph can then be repeated three additional times. The sheet can then be rinsed with deionized water, boiled in HCl for 10 minutes, rinsed with deionized water and dried.

The polymer base can be dissolved in solvents, for example dimethyl acetamide, acetone, methylethyle ketone, toluene, dimethyl carbonate, diethyl carbonate, and combinations thereof. The solvent can then be allowed to dry, producing a thin film. While the solution is wet, a low friction (e.g., glass, Teflon) plate can be dipped into the solution and removed. The coating on the plate can dry, creating a thin film. The plate can be repeatedly dipped into the solution to increase the thickness of the film.

Figure 25:
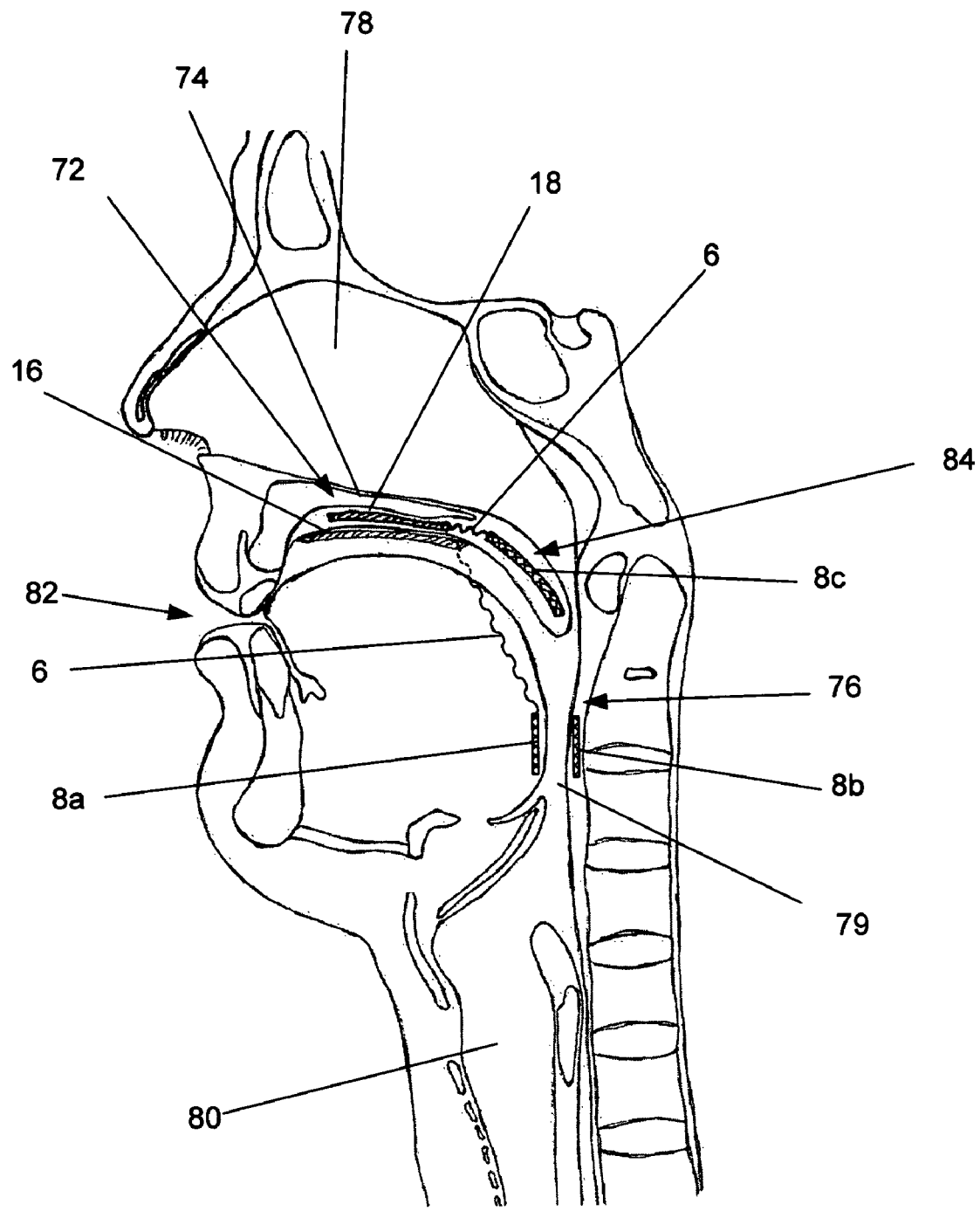
FIG. 25 shows a sagittal section through a head of a subject illustrating an embodiment of a method for using the patency system.

Polyvinyl alcohol, polyvinyl pyrrolidone, polyvinyl acetate or combinations thereof can be added to a PVDF solution before drying, thus contributing hydrophilic properties to PVDF and can improve ion migration through the polymer film during manufacture. Dye or other color pigments can be added to the polymer solution Method of Using FIG. 25 illustrates that the first inductor 18 can be implanted in the mouth roof 72, for example in or adjacent to the hard palate 74. Wire leads 6 can connect the first inductor 18 to the patency elements 8. A first patency element 8a can be implanted in the base of the tongue at the pharynx wall 76. A second patency element 8b can be integral with the first patency element 8a (e.g., as two sections of a hollow cylindrical patency element 8, such as shown in FIG. 17). The first and second patency elements 8a and 8b can be separate and unattached elements. The third patency element 8c can be implanted in the uvula and/or soft palate 84. The patency elements 8 can also be implanted in the wall of the nasal passages 78, higher or lower in the pharynx 79, such as in the nasal pharynx, in the wall of the trachea 80, in the larynx (not shown), in any other airway, or combinations thereof.

The second inductor 16 can be worn by the patient in the mouth 82. The second inductor 16 can be connected to an integral or non-integral power supply. The second inductor 16 can be one or multiple induction coils. The second inductor 16 can inductively transmit RF energy to the first inductor 18. The first inductor 18 can change the RF energy into electricity. The first inductor 18 can send a charge or current along the wire leads 6 to the patency elements 8. The patency elements 8 can be energized by the charge or current. The energized patency elements 8 can increase the stiffness and/or alter the shape of the patency elements 8. The energized patency elements 8 can create and or maintain patency of the airway around which the patency elements 8 are implanted.

The non-energized patency elements 8 can be configured to conform to the airway around which the patency elements 8 are implanted. The non-energized patency elements 8 can be flexible and soft.

Figure 26:
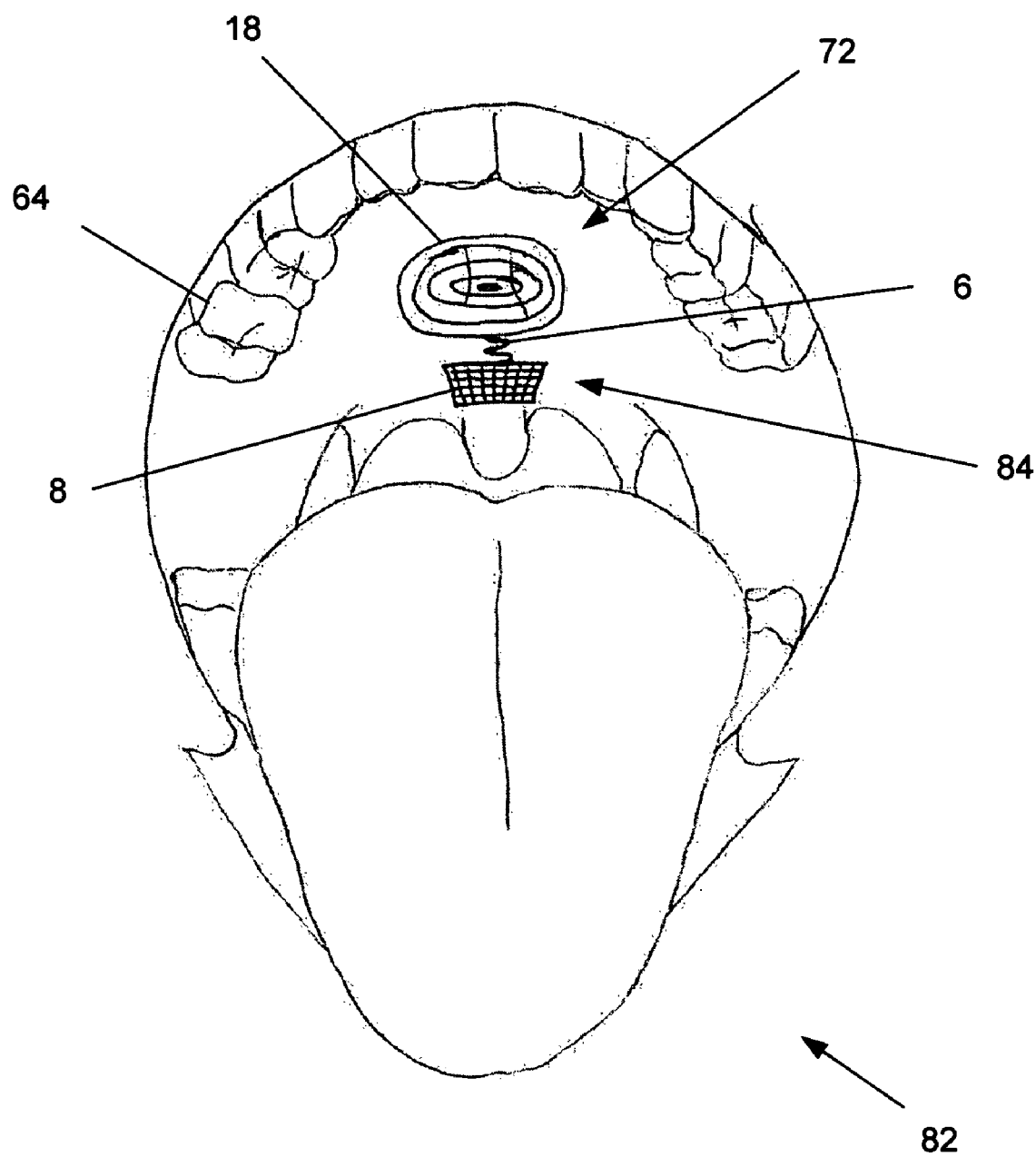
FIG. 26 through 29 illustrate anterior views of the mouth with see-though mouth roofs of various embodiments of methods for using the patency system.

FIG. 26 illustrates that the first inductor 18 can be implanted in the mouth roof 72 and attached to a single patency element 8 via the wire lead 6. The patency element 8 can be in the soft palate 84, or elsewhere.

Figure 27:
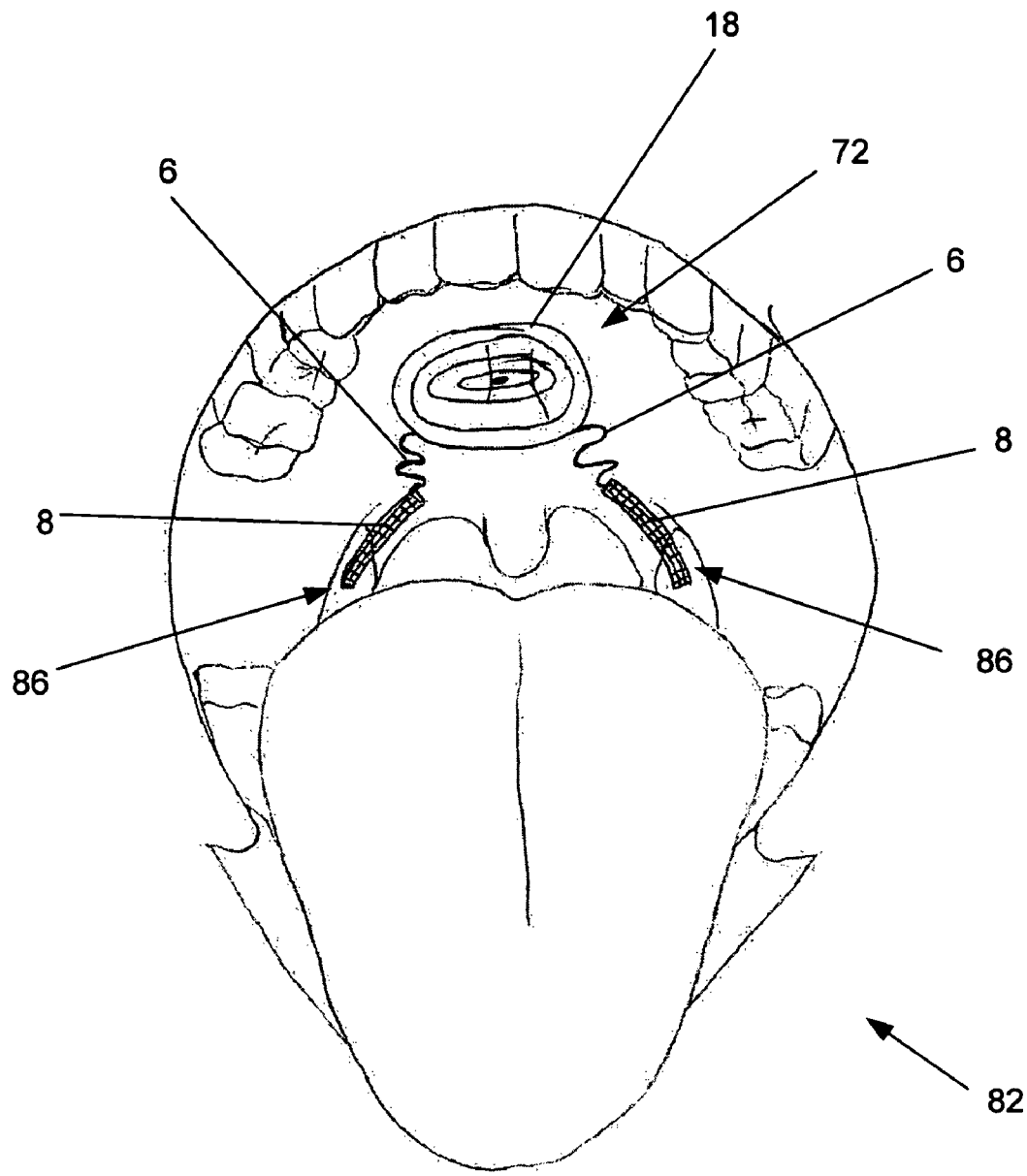

FIG. 27 illustrates that the first inductor 18 can be implanted in the mouth roof 72 and attached to two patency elements 8 via two wire leads 6. The patency elements 8 can be implanted in side walls 86 of the mouth 82.

Figure 28:
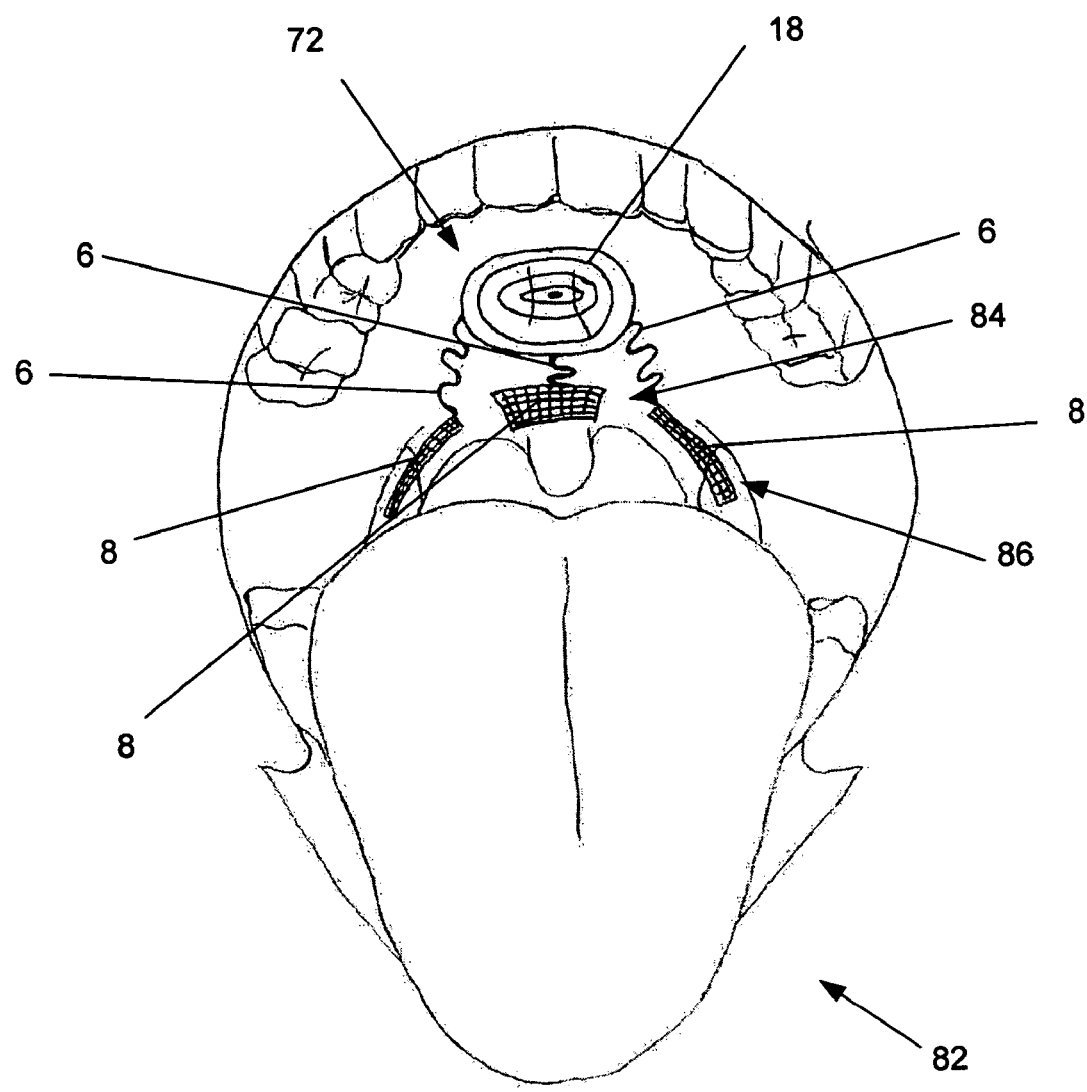

FIG. 28 illustrates that the first inductor 18 can be implanted in the mouth roof 72 and attached to three patency elements 8 via three wire leads 6. The patency elements 8 can be implanted in the soft palate 84 and the side walls 86 of the mouth 82

Figure 29:
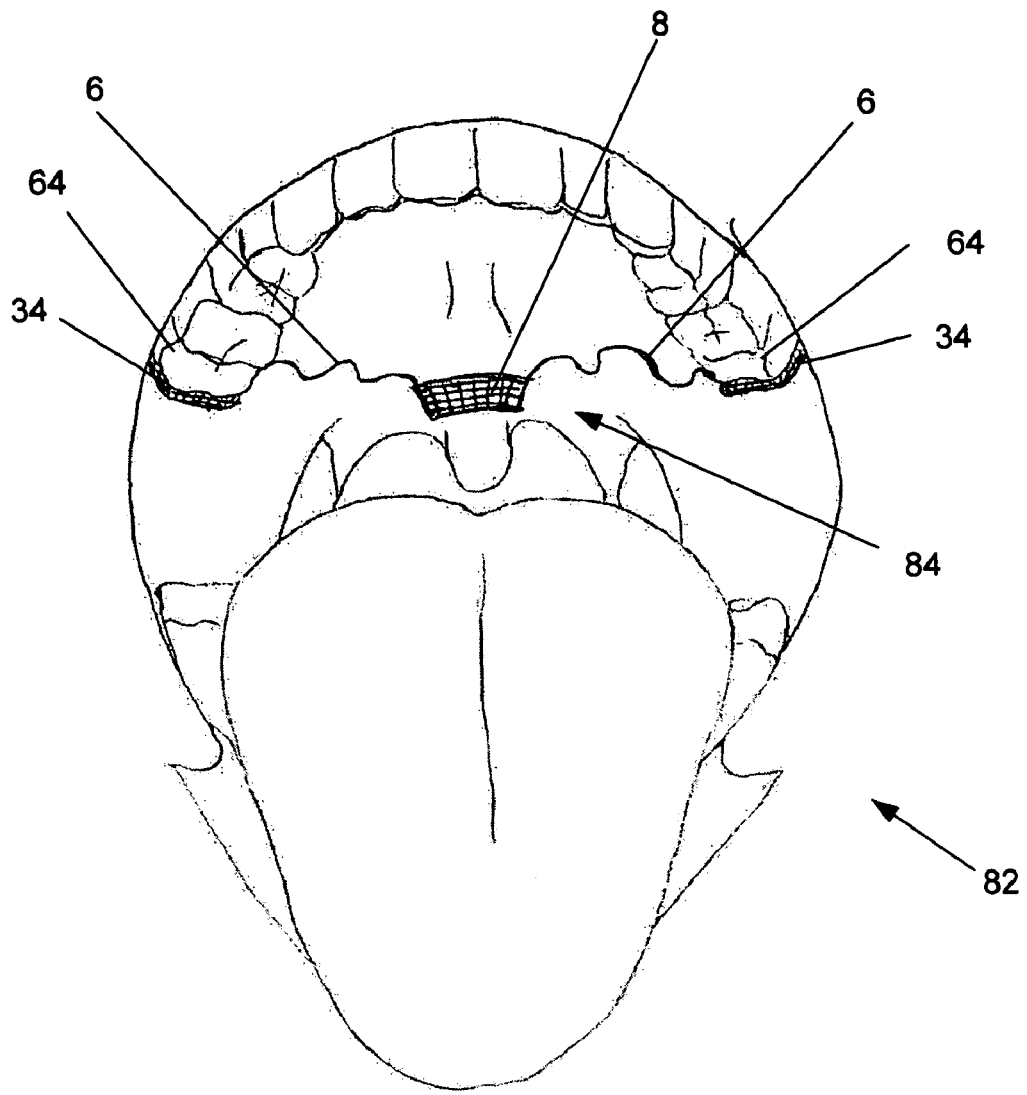

FIG. 29 illustrates that the first conductors 34 (not shown, e.g., the tooth sockets 68), can be attached to, and in conductive electrical communication with, the second conductors 36. The retainer 66, such as shown in FIG. 23, can be worn by the patient to energize the patency element 8. The tooth sockets 68 can removably attach to the first conductors 34. The first conductors 34 can be dental fillings 62, conductive posts adjacent to and/or through the teeth 64.

Figure 30:
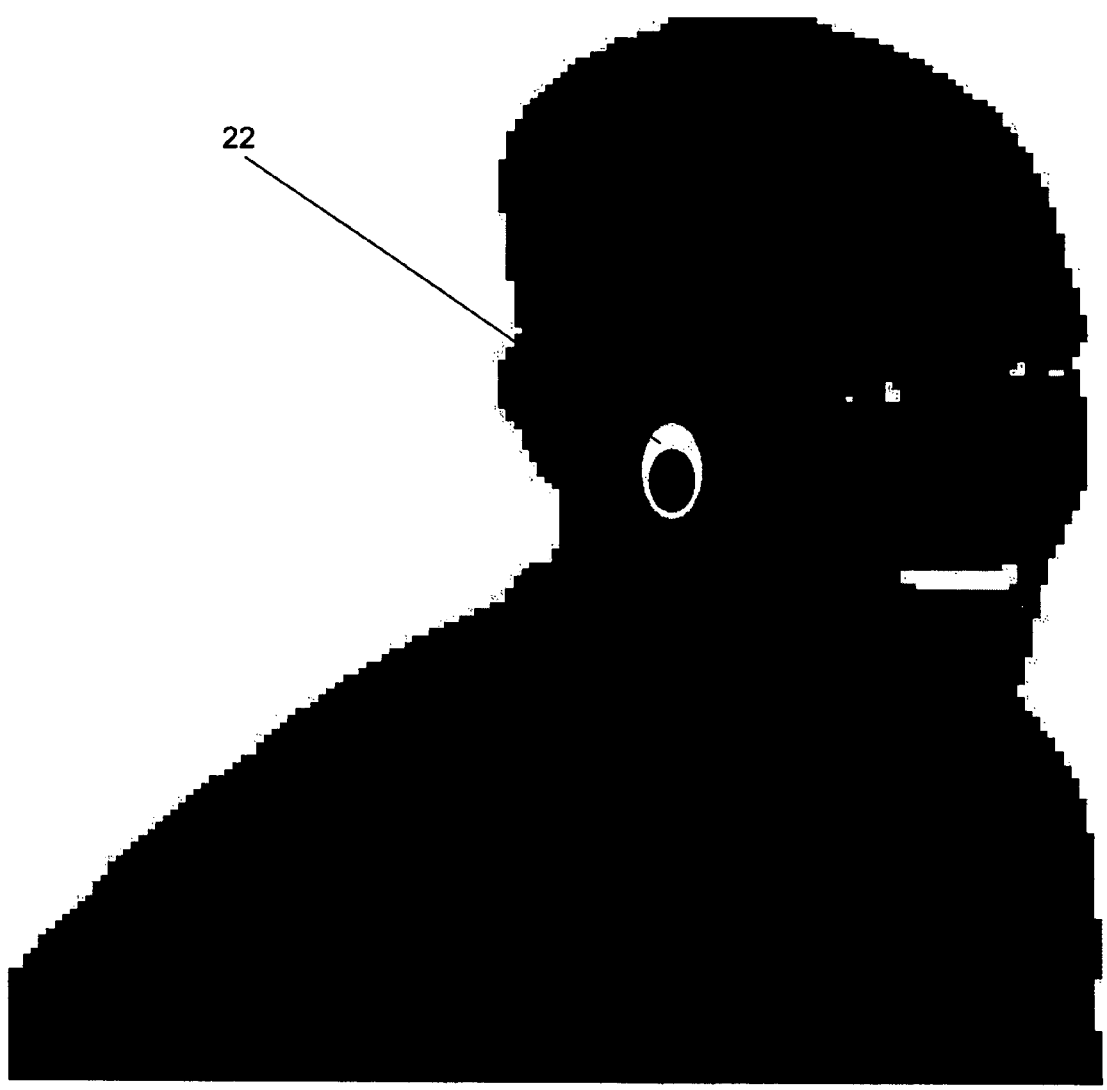
FIG. 30 illustrates an embodiment of a method for using the patency system.

FIG. 30 illustrates that a patient 88 with the first transducer (not shown) implanted in the patient's cheek can wear the non-implanted portion 22, such as shown in FIG. 24, on the outside of the patient's cheek. The non-implanted portion 22 can energize the implanted portion 20.

It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

We claim:

1. A system for maintaining airway patency in a biological subject comprising:
   an implantable anode;
   an implantable cathode;
   an implantable patency element connected with the anode and the cathode, said implantable patency element being adapted and configured for implantation in a subject's airway;
   an implantable transducer connected with the anode and the cathode;
   a removable transducer configured to transfer energy to the implantable transducer; and
   a removable power source connected with the removable transducer;
   wherein the implantable patency element comprises an implantable electroactive polymer configured to modulate a shape of the subject's airway when the implantable patency element is energized.

2. The system of claim 1, further comprising a removable pulse-width modulation circuit.

3. The system of claim 1 wherein the removable transducer and the removable power source are in a mouthpiece.

4. The system of claim 1, wherein the removable transducer and the removable power source are in a dermal patch.

5. The system of claim 1, wherein the implantable patency element comprises an ion exchange polymer metal composite material.

6. The system of claim 5, wherein the implantable patency element comprises an ionomer and a conductive material.

7. The system of claim 6, wherein the ionomer comprising perfluorinated polymer.

8. The system of claim 6, wherein the ionomer comprises polytetrafluoroethylene.

9. The system of claim 6, wherein the ionomer comprises polyfluorosulfonic acid.

10. The system of claim 6, wherein the ionomer comprises perfluorosulfonate.

11. The system of claim 6, wherein the ionomer comprises polyvinylidene fluoride.

12. The system of claim 6, wherein the ionomer comprises hydrophilic polyvinylidene fluoride.

13. The system of claim 6, wherein the ionomer comprises polyethylene.

14. The system of claim 6, wherein the ionomer comprises polypropylene.

15. The system of claim 6, wherein the ionomer comprises polystyrene.

16. The system of claim 6, wherein the ionomer comprises polyaniline.

17. The system of claim 6, wherein the ionomer comprises polyacrylonitrile.

18. The system of claim 6, wherein the ionomer comprises cellophane.

19. The system of claim 6, wherein the ionomer comprises cellulose.

20. The system of claim 6, wherein the ionomer comprises regenerated cellulose.

21. The system of claim 6, wherein the ionomer comprises cellulose acetate.

22. The system of claim 6, wherein the ionomer comprises polysulfone.

23. The system of claim 6, wherein the ionomer comprises polyurethane.

24. The system of claim 6, wherein the ionomer comprises polyvinyl alcohol.

25. The system of claim 6, wherein the ionomer comprises polyvinyl acetate.

26. The system of claim 6, wherein the ionomer comprises polyvinyl pyrrolidone.

27. The system of claim 6, wherein the conductive material comprises platinum.

28. The system of claim 6, wherein the conductive material comprises gold.

29. The system of claim 6, wherein the conductive material comprises silver.

30. The system of claim 6, wherein the conductive material comprises palladium.

31. The system of claim 6, wherein the conductive material comprises copper.

32. The system of claim 6, wherein the conductive material comprises carbon.

33. The system of claim 1, further comprising a coating.

34. The system of claim 33, wherein the coating is on an implantable patency element and/or an implantable transducer and/or an implantable lead wire connecting the patency element and the implantable transducer.

35. The system of claim 33, wherein the coating is only on the implantable patency element.

36. The system of claim 33, wherein the coating comprises a dielectric coating.

37. The system of claim 36, wherein the dielectric coating comprises silicone.

38. The system of claim 36, wherein the dielectric coating comprises polyurethane.

39. The system of claim 36, wherein the dielectric coating comprises polyimide.

40. The system of claim 36, wherein the dielectric coating comprises nylon.

41. The system of claim 36, wherein the dielectric coating comprises polyester.

42. The system of claim 36, wherein the dielectric coating comprises polymethylmethacrylate.

43. The system of claim 36, wherein the dielectric coating comprises polyethylmethacrylate.

44. The system of claim 36, wherein the dielectric coating comprises neoprene.

45. The system of claim 36, wherein the dielectric coating comprises styrene butadiene styrene.

46. The system of claim 33, wherein the dielectric coating comprises polyvinyl acetate.

47. The system of claim 33, wherein the coating comprises a tissue growth promoting material.

48. The system of claim 47, wherein the tissue growth promoting material comprises poly-L lysine.

49. The system of claim 47, wherein the tissue growth promoting material comprises poly-D lysine.

50. The system of claim 47, wherein the tissue growth promoting material comprises polyethylene glycol.

51. The system of claim 47, wherein the tissue growth promoting material comprises polyvinyl alcohol.

52. The system of claim 47, wherein the tissue growth promoting material comprises polyvinyl acetate.

53. The system of claim 47, wherein the tissue growth promoting material comprises hyaluronic acid.

54. The system of claim 47, wherein the tissue growth promoting material comprises methylmethacrylate.

55. The system of claim 33, wherein the coating comprises a tissue growth preventing material.

56. The system of claim 55, wherein the tissue growth preventing material comprises polypropylene.

57. The system of claim 55, wherein the tissue growth preventing material comprises polyethylene.

58. The system of claim 55, wherein the tissue growth preventing material comprises polyvinylidene fluoride.

59. The system of claim 1, further comprising a battery charger.

* * * * *